United States Patent [19]

Mueller et al.

[11] Patent Number: 4,711,903
[45] Date of Patent: Dec. 8, 1987

[54] PHENOLIC THIOETHERS AS INHIBITORS OF 5-LIPOXYGENASE

[75] Inventors: Richard A. Mueller, Glencoe; Richard A. Partis, Evanston; James R. Deason, Wilmette, all of Ill.

[73] Assignee: G. D. Searle & Co., Chicago, Ill.

[21] Appl. No.: 824,984

[22] Filed: Jan. 31, 1986

[51] Int. Cl.$^4$ .................... C07C 149/40; A61K 37/10
[52] U.S. Cl. ........................ 514/381; 514/532; 514/539; 514/548; 514/562; 514/570; 514/571; 548/252; 560/11; 560/12; 560/17; 560/138; 560/141; 562/429; 562/430; 562/431
[58] Field of Search ............... 560/11, 12, 15, 17, 560/138, 141; 562/429, 430, 431; 514/381, 539, 532, 562, 570, 571, 548; 548/252

[56] References Cited

U.S. PATENT DOCUMENTS

| | | | |
|---|---|---|---|
| 4,029,812 | 6/1977 | Wagner et al. | 424/298 |
| 4,076,841 | 2/1978 | Wagner et al. | 424/324 |
| 4,078,084 | 3/1978 | Wagner et al. | 424/324 |
| 4,153,803 | 5/1979 | Thiele et al. | 564/162 |

FOREIGN PATENT DOCUMENTS 0131221  1/1985  European Pat. Off. .

OTHER PUBLICATIONS

"Typical Methods for Obtaining Stabilizers Containing Sulfur", *Khimiya; Khimicheskaya Tekhnologiya*, Medvedv et al. (1977); pp. 568–574, (Translation).

*Primary Examiner*—Michael L. Shippen
*Attorney, Agent, or Firm*—Mary Jo Kanady; Paul D. Matukaitis

[57] ABSTRACT

The compounds of the present invention comprise substituted phenolic thioethers represented by the formula:

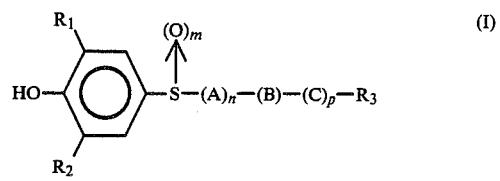

wherein: $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl or a tetrazole group; m is 0 or 1, n is 2, 3 or 4 and p is 1, 2 or 3; amd the pharmaceutically acceptable salts thereof. The compounds of the present invention are specific inhibitors of 5-lipoxygenase and, therefore, are useful in the treatment of local and systemic inflammation, allergy and hypersensitivity reactions and other disorders in which agents formed in the 5-lipoxygenase metabolic pathway are involved.

20 Claims, No Drawings

PHENOLIC THIOETHERS AS INHIBITORS OF 5-LIPOXYGENASE

BACKGROUND OF THE INVENTION

The present invention relates to substituted phenolic thioethers and more particularly relates to the novel compounds of formula I which are specific 5-lipoxygenase inhibitors and are useful, for example, as anti-inflammatory and anti-allergy agents.

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetranenoic acids (HPETEs) and the leukotrienes, all of which have potent physiological effects. The leukotrienes, which are produced via the 5-lipoxygenase pathway, are the major contributors to the onset of the symptoms of asthma, and mediators for immediate hypersensitivity reactions, inflammation and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of $LTB_4$. $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, antipyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects. Administration of the NSAIDs alone can produce allergic reactions including bronchospastic reactivity; skin rashes; syndrome of abdominal pain, fever, chills, nausea and vomiting; and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs. Co-administration of the 5-lipoxygenase inhibitors of this invention with cyclooxygenase inhibitors may mitigate the untoward side effects of the latter and allow the increased advantageous use of such cyclooxygenase inhibitors.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides new chemical entities which are inhibitors of the 5-lipoxygenase pathway and are useful in the treatment of asthma, rheumatoid arthritis, psoriasis, and other allergic, hypersensitivity, and inflammatory conditions.

See Bengt Samuesson, "Leukotrienes: Mediators of Immediate Hypersensitivity Reactions and Inflammation", *Science*, Vol. 220, pp. 568–575 (May 1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York 1984); Editorial, "Leukotrienes and other Lipoxygenase Products in the Pathogenesis and Therapy of Psoriasis and Dermatoses", *Arch. Dermatol*, Vol. 119, pp 541–547 (July, 1983); Robert A. Lewis et al., "A Review of Recent Contributions on Biologically active Products of Arachidonate Conversion", *Int. J. Immunopharmac.*, Vol. 4, No. 2, pp 85–90 (1982); Michael K. Bach, *Biochemical Pharmacology*, Vol. 23, No. 4, pp 515–421 (1984); and E. L. Becker, *Chemotactic Factors of Inflammation*, pp 223–225 (Elsevier Science Publishers V.B., Amsterdam, 1983); P. Sharon, and W. F. Stenson, *Gastroenterology*, Vol. 84, 454 (1984); and Musch, M. W. et al., *Science*, Vol. 217, 1255 (1982).

The present invention provides compounds which block the 5-lipoxygenase metabolic pathway and, therefore, block the formation of the leukotrienes responsible for allergy and inflammation, and represent therapeutic agents which are useful in the treatment of allergic and hypersensitivity reactions and inflammation, alone, or also may be utilized in combination with other lipoxygenase inhibitors or with cyclooxygenase inhibitors such as the non-steroidal anti-inflammatory agents.

Various thioether compounds have been described previously. For example, European Patent Application publication No. 0131221 discloses compounds of the formula

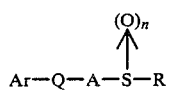

in which Ar is phenyl or phenyl substituted by one to three of varied substituents, for example, alkyl, alkoxy, hydroxy, etc.; Q is oxygen, sulfur or an NH group; A is straight or branched chain, optionally substituted, alkylene and R is hydrogen or straight or branched alkyl, optionally substituted by alkoxy, hydroxyl, carboxyl, alkoxycarbonyl, etc.; and n is 0, 1 or 2. The disclosed compounds are indicated to have anti-inflammatory and anti-allergic properties through inhibition of undefined anaphylactic and anaphylactoid reactions, although no test data are provided. The preferred compounds are stated to be those in which Q represents oxygen and n is 0 without mention of any preference among the numerous possible substituents for R or substituted phenyl as Ar. In contrast to the invention disclosed in the foregoing publication, the compounds of the present invention all have a sulfur atom at the position corresponding to Q as well as having di(tertiary)-alkyl or diphenyl groups as substituents on the phenol moiety corresponding to the substituted Ar group in the above publication which, as described therein, amy or may not comprise a phenol. Moreover, it is noted that the compounds of the present invention have been found to possess specificity for the inhibition of 5-lipoxygenase which is an important distinctive property not attributed to the compounds in the foregoing publication. Those of ordinary skill in the art will appreciate that the compounds of formula I of this invention, including their surprising specific 5-lipoxygenase inhibitory properties, are, therefore, not specifically described in the aforementioned EPA publication No. 0131221.

U.S. Pat. Nos. 4,029,812, 4,076,841 and 4,078,084 disclose compounds of the formula

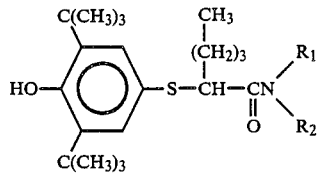

comprising 2-(3,5-di-tert-butyl-4-hydroxy-phenyl)thio carboxamides. The compounds are indicated to be useful in lowering serum cholesterol and triglyceride levels.

A series of thioethers, useful as, for example, polyfunctional antioxidants for polymers, and biologically active substances, obtained by the nucleophilic addition of thiols, including 3,5-di-tert-butyl-4-hydroxythiophenol, and hydrogen sulfide to acrylate derivatives have been described. See Medvedev et al., *Khimiya; Khimicheskaya Tekhnologiya,* Volume 20, (1977), pp. 568-574. The compounds resulting from the foregoing process have the general formulas $RS(CH_2)_nX$ and $S(CH_2CH_2X)_2$ in which R is 3,5-di-tert-butyl-4-hydroxyphenyl and X represents, for example, $-C\equiv N$, $NH_2$, $CH(OH)CH_2Cl$, OH, COCl and various carboxy, carboxylate and amide functions. Compounds of formula I according to the present invention or 5-lipoxygenase activity for structurally related compounds are not disclosed.

U.S. Pat. No. 4,153,803 discloses cholesterol-lowering phenoxyalkanoic acid esters of the formula

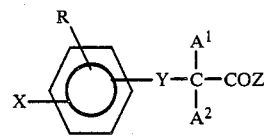

wherein, when Y is sulfur, X is hydrogen, benzyl, benzyloxy or benzylthio or substituted derivatives thereof; R is hydrogen, halogen, hydroxy, alkyl or alkoxy, $A^1$ and $A^2$ are hydrogen or alkyl and Z is amine or azacyclohydrocarbonyloxy.

SUMMARY OF THE INVENTION

It is, therefore, a primary object of the present invention to provide novel substituted phenolic thioethers.

It is a further object of the present invention to provide methods for promoting anti-allergic and anti-inflammatory effects in mammals in need thereof by the administration of preselected dosages of the compounds of the present invention or pharmaceutically acceptable salts thereof in appropriate non-toxic pharmaceutical dosage forms or compositions.

Another object of the present invention is to provide dosage unit forms adapted for, e.g., oral and/or parenteral administration and useful in the treatment, management and mitigation of allergies, inflammation and hypersensitivity reactions and related disorders and conditions in which physiologically active agents formed in the 5-lipoxygenase metabolic pathway are involved.

DETAILED DESCRIPTION OF THE PREFERRED EMBODIMENTS

These and other similar objects, advantages and features are accomplished according to the products, compositions and methods of the invention comprised of compounds of the formula

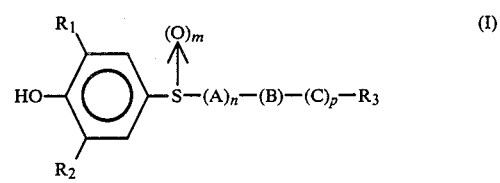

and the pharmaceutically acceptable salts thereof wherein $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl or a tetrazole group; m is 0 or 1, n is 2, 3 or 4 and p is 1, 2 or 3.

The term "tert-alkyl" as used herein in reference to $R_1$ and $R_2$ refers to branched chain alkyl moieties of from about 4 to 10 carbon atoms having a tertiary carbon atom attached to the phenyl ring substituted by $R_1$ and $R_2$. Exemplary of such groups are tert-butyl, i.e., 1,1-dimethylethyl, 1-1-dimethylpropyl, 1-methyl-1-(ethyl)pentyl, 1,1-diethylpropyl, 1-ethyl-1-(propyl)butyl and the like.

The term "alkyl" defines straight or branched chain monovalent hydrocarbon radicals having between about 1 to 6 carbon atoms including, for example, methyl, ethyl, propyl, pentyl, 1-methylbutyl, isopentyl, neopentyl, etc.

As used herein, "substituted phenyl" and "substituted benzyl" defines those derivatives wherein the phenyl moiety thereof is substituted by one or two substituents which may be the same or different and independently selected from halogen (i.e., chlorine, bromine or fluorine), $C_1$–$C_6$ alkyl, hydroxy, $C_1$–$C_6$ alkoxy, acetoxy, carboxylic acid and $C_1$–$C_6$ alkyl esters thereof, nitro or phenyl.

The N-substituted phenyl or N-substituted benzyl moieties set forth above are described in U.S. Pat. No. 4551279, the disclosure of which is incorporated herein by reference. Such moieties include, for example, N-phenylglycine ethyl ester, N-(4-chlorophenyl)glycine ethyl ester, N-(4-hydroxyphenyl)glycine, etc. Methods for their preparation are also described in detail in the aforesaid patent. These nitrogen substituted compounds are utilized as reactants to prepare the compounds of the present invention of formula I according to the synthesis procedures set forth below.

It will be appreciated by those skilled in the art that when A or C in formula I represents substituted methylene, an asymmetric center exists and accordingly, d and l enantiomers or diastereomers and mixtures are obtained. The present invention includes such mixtures as well as the separate isomers.

Representative of preferred compounds of formula I are those wherein $R_1$ and $R_2$ are both tert-alkyl or phenyl; A is —$CH_2$—$CH_2$— or

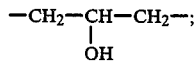

B is sulfur; C is —$CH_2$— or —$CH_2$—$CH_2$—; $R_3$ is $CO_2H$ (or $CO_2^-$ + cation) and m is O.

Especially preferred for use in the therapeutic methods of the invention are compounds of the formulae:

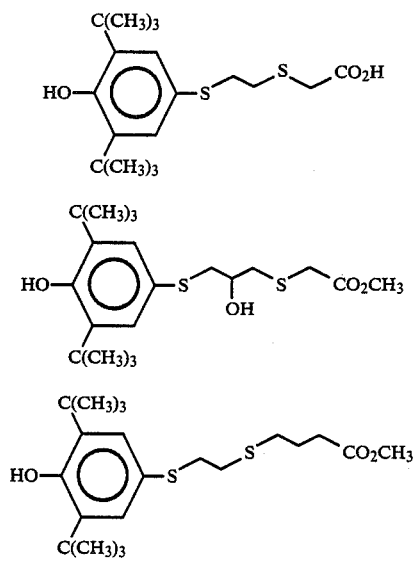

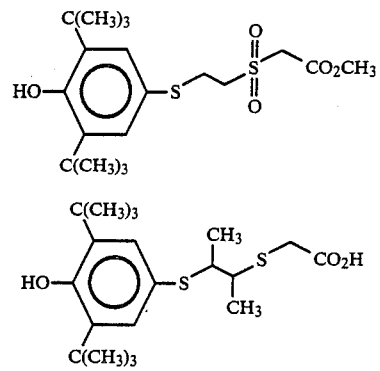

The expression "pharmaceutically acceptable salts" is intended to include those salts capable of being formed with the compounds of the present invention, e.g., when $R_3$ represents carboxyl or tetrazole, without materially altering the chemical structure or pharmacological properties thereof. Such salts include inorganic and organic cations or acid addition salts, such as sodium, potassium, calcium, ammonium, alkylammonium, triethanolamine, lysine, hydrochloric, hydrobromide, etc. well known to those skilled in the art. The foregoing salts are prepared in the conventional manner by neutralization of the compounds of formula I with the desired base or acid.

The compounds of the present invention can be administered in such oral dosage forms as tablets, capsules, pills, powders, granules, elixirs, or syrups as well as aerosols for inhalation. Likewise, administration may be effected intravascularly, subcutaneously, or intramuscularly using dosage forms known to those or ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the condition. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically to treat proliferative skin conditions such as psoriasis. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of the invention are easily prepared from readily available starting materials by any of the following alternate processes in a conventional manner. The following reaction schemes describe the methods employed for preparing the compounds of formula I, including starting materials, intermediates, and reaction conditions.

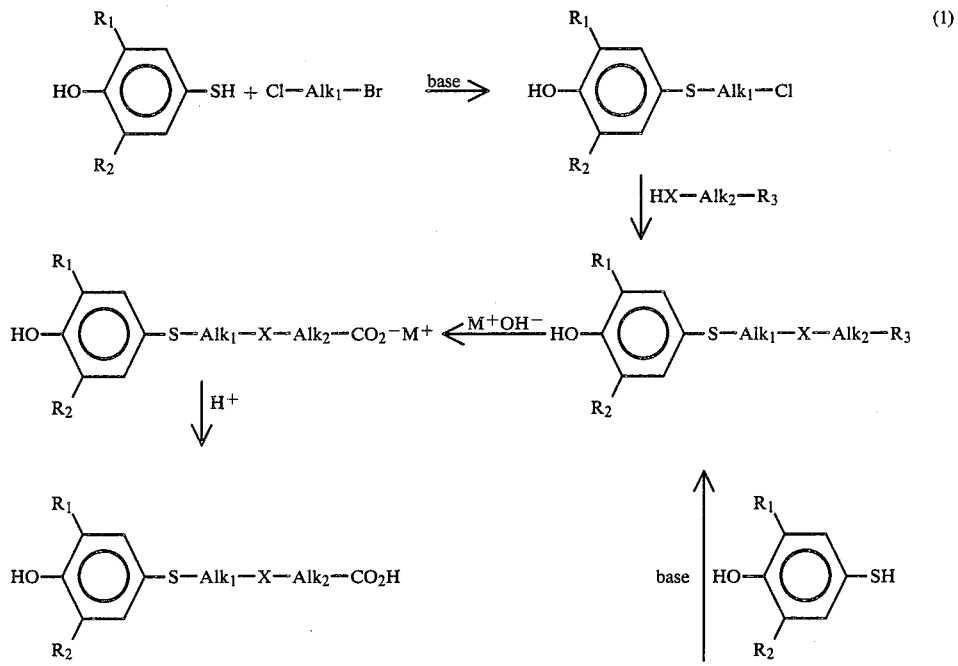

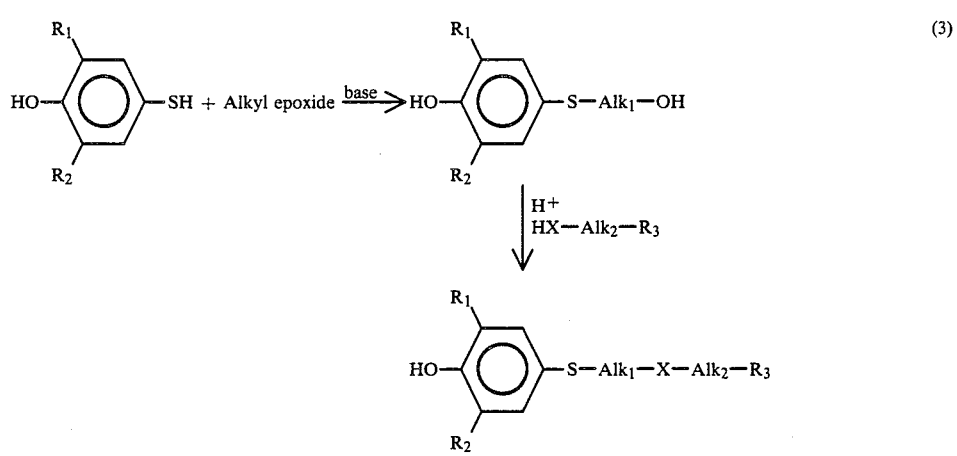

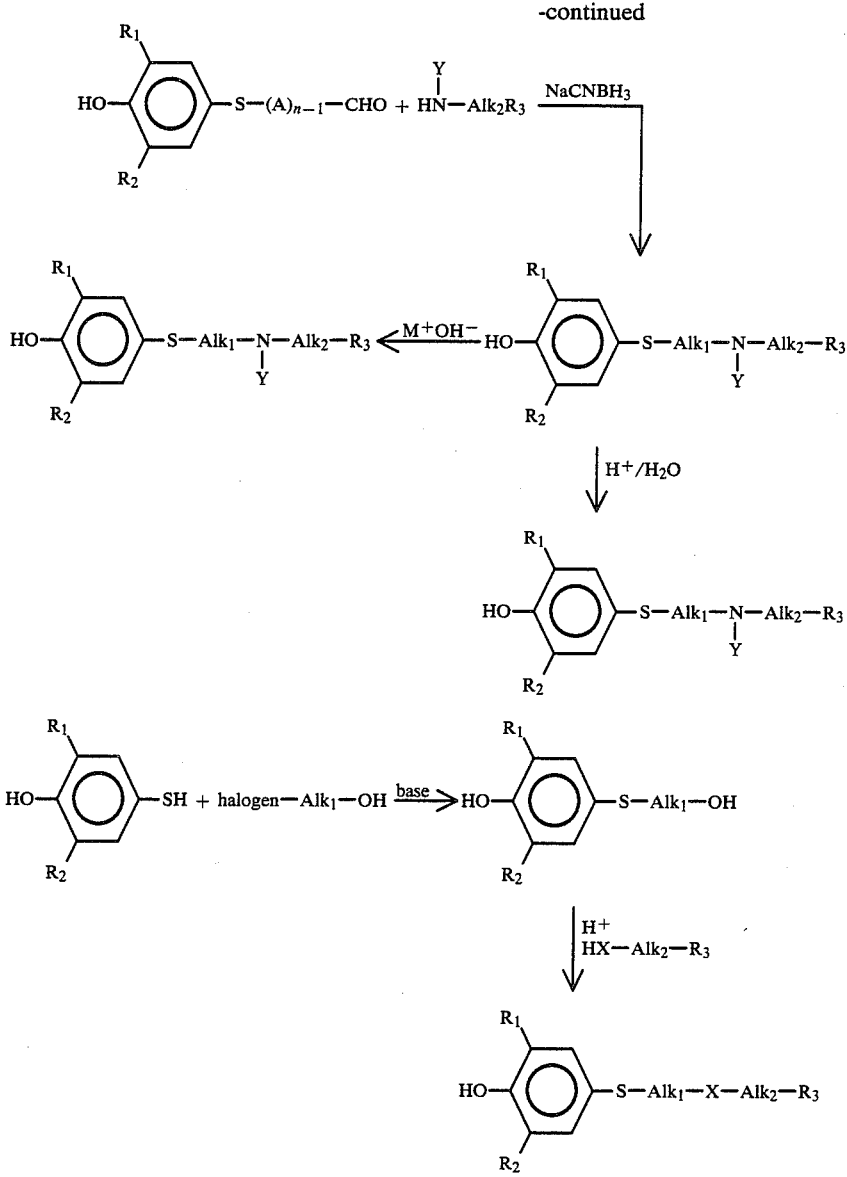

In the above formulas, $R_1$ and $R_2$ are as defined before. $R_3$ is $CO_2H$ or $CO_2$-alkyl. $Alk_1$ is straight or branched alkyl or hydroxyalkyl. $Alk_2$ is straight or branched alkyl. $M^+$ is $Li^+$, $Na^+$, $K^+$, $^+N(R_4)_4$ in which $R_4$ is hydrogen or straight or branched alkyl. Alkyl epoxide is

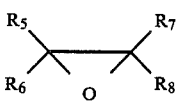

in which $R_5$-$R_8$ represent hydrogen, straight or branched alkyl. X represents B as defined before. Y represents hydrogen, alkyl, phenyl, benzyl, substituted phenyl or substituted benzyl.

The following non-limiting examples further illustrate details for the preparation of the compounds of the present invention. Those skilled in the art will readily understand and appreciate that known variations of the conditions and procedures in the following preparative methods can be utilized. All temperatures are degrees Celcius unless otherwise noted. Melting points were determined on a Thomas-Hoover melting point apparatus and are uncorrected.

EXAMPLE 1

3,5-bis(1,1-dimethylethyl)-4-hydroxyphenyl thiocyanate

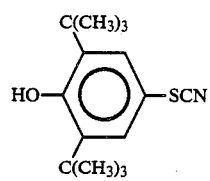

To a three-necked, round bottom 5 L flask, equipped with a mechanical stirrer, gas inlet, thermometer and gas inlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1 and ½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated by addition of water, filtered and dried for 2 days over phosphorous pentoxide. The resulting gummy yellow solid was recrystallized from pentane and dried in vacuo to yield the product as a white powder, m.p. 61.5°-63° C.

Analysis calc. for $C_{15}H_{21}NSO$: Theory: C, 68.40; H, 8.03; N, 5.32; S, 12.17. Found: C, 68.85; H, 8.05; N, 5.29; S, 12.12.

EXAMPLE 2

2,6-bis(1,1-dimethylethyl)-4-mercaptophenol

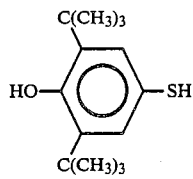

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3

[[2-[[3,5-bis(1,1-dimethylethyl)-4-hydroxyphenyl]thio]ethyl]thio]acetic acid, monosodium salt

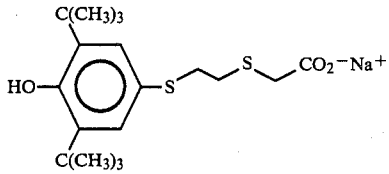

Mercaptoacetic acid (1.3 g, 0.0144 mole) was added to a solution of sodium ethoxide, prepared from sodium (0.66 g, 0.0288 mole) in ethyl alcohol (25 ml). After stirring for one hour, 1-bromo-2-chloroethane (6 ml, 0.072 mole) was added all at once and the solution stirred for 2 hours. After refluxing for 4 hours, the excess 1-bromo-2-chloro ethane was removed by rotary evaporator. Ethyl alcohol (50 ml) was added to the residue and the sodium salt of 2,6-bis(1,1-dimethylethyl)-4-mercaptophenol prepared from sodium (0.33 g, 0.0144 mole) and 2,6-bis(1,1-dimethylethyl)-4-mercaptophenol (3.43 g, 0.0144 mole) in ethyl alcohol (25 ml) was added by cannula. After stirring for eighteen hours at room temperature, the mixture was refluxed for 1 hour, cooled to room temperature and water (50 ml) added with rapid stirring. The ethyl alcohol was removed with a rotary evaporator. The aqueous residue was extracted with ethyl acetate (2×100 ml) combined, dried over sodium sulfate, filtered and concentrated. The residue was crystallized from ethyl acetate/hexane. This solid was recrystallized from ethyl acetate/hexane to give the title compound.

Analysis calc. for $C_{18}H_{27}O_3S_2Na$ (378.54): Calc.: C, 57.11; H, 7.19; S, 16.94. Found: C, 56.75; H, 7.24; S, 16.84.

EXAMPLE 4

[[2-[[3,5-bis(1,1-dimethylethyl)-4-hydroxyphenyl]thio]ethyl]thio]acetic acid

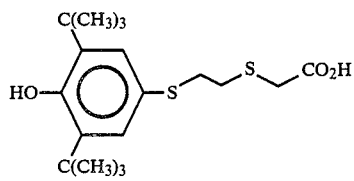

The title compound of Example 3 (0.90 g) was dissolved in water (40 ml) acidified with 10% hydrochloric acid and extracted into ethyl acetate (2×50 ml). The combined extracts were dried over sodium sulfate, filtered and concentrated using a rotary evaporator to give an oil. The oil was crystallized from hexane to give the title compound, m.p. ca. 86° C.

Analysis calc. for $C_{18}H_{28}O_3S_2$ (356.54): Calc.: C, 60.64; H, 7.92; S, 17.98. Found: C, 60.93; H, 7.87; S, 17.81.

EXAMPLE 5

The title compound of Example 4 was also prepared by the procedure of Example 3 without the isolation of the sodium salt. The ethyl acetate solution containing the sodium salt was treated with ten percent hydrochloric acid, stirred for thirty minutes and the layers were separated. The organic layer was dried over sodium sulfate, filtered and concentrated with a rotary evaporator to give a solid which was recrystallized from hexane.

Analysis calc. for $C_{18}H_{28}O_3S_2$ (356.54): Calc.: C, 60.64; H, 7.92; S, 17.98. Found: C, 60.73; H, 7.84; S, 17.92.

EXAMPLE 6

[[2-[[3,5-bis(1,1-dimethylethyl)-4-hydroxyphenyl]thio]ethyl]thio]acetic acid, 2,2',2"nitrilotris[ethanol]salt

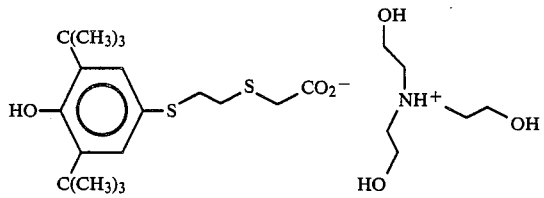

A solution of triethanol amine (0.60 g, 0.004 mole) in ethyl alcohol (3 ml) was added to a solution of the title compound of Example 4 (1.4 g, 0.004 mole) in ethyl alcohol (5 ml). This mixture was heated on a hot plate for 1.5 hours. The ethyl alcohol solution was concentrated to a volume of 5 ml and ethyl ether (25 ml) was added followed by hexane (5 ml). A white solid was filtered, washed with ethyl ether—hexane and air dried to give 1.8 g of the title compound, m.p. ca. 81° C.

Analysis calc. for $C_{24}H_{43}NO_6S_2$ (505.7): Calc.: C, 57.00; H, 8.57; N, 2.77; S, 12.68. Found: C, 56.94; H, 8.53; N, 2.76; S, 12.60.

EXAMPLE 7

[[2-[[3,5-bis(1,1-dimethylethyl)-4-hydroxyphenyl]thio]ethyl]thio]acetic acid, lysine salt

[Structure: 2,6-di-tert-butyl-4-hydroxyphenyl-S-CH₂CH₂-S-CH₂-CO₂⁻ H₃N⁺—CO₂H with (CH₂)₄—NH₂ side chain]

The title compound of Example 4 (0.71 g, 0.002 mole) and lysine (0.29 g, 0.002 mole) were dissolved in methyl alcohol (30 ml) and heated at 40° C. for 18 hrs. The solution was concentrated to a volume of 15 ml and ethyl ether added until cloudy and cooled for 72 hrs in a refrigerator. The white solid was filtered, washed well with ethyl ether, and dried in vacuo to give 0.59 g of the product, m.p. ca. 130° C.

Analysis calc. for $C_{24}H_{42}N_2O_5S_2$ (502.7): Calc.: C, 57.34; H, 8.42; N, 5.57. Found: C, 57.41; H, 8.14; N, 5.69.

EXAMPLE 8 methyl[[2-[[3,5-bis(1,1-dimethylethyl)-4-hydroxyphenyl]thio]ethyl]thio]acetate

[Structure: 2,6-di-tert-butyl-4-hydroxyphenyl-S-CH₂CH₂-S-CH₂-CO₂CH₃]

Thionyl chloride (3 ml) was added to the title compound of Example 4 (1.2 g, 0.003 mole) in methyl alcohol (50 ml) and stirred for 2 hours. The solvent and excess thionyl chloride were removed using a rotary evaporator and the product purified by chromatography on silica to give 0.8 g of an oil.

Analysis calc. for $C_{19}H_{30}O_3S_2$ (370.5): Calc.: C, 61.58; H, 8.16; S, 17.30. Found: C, 61.46; H, 8.04; S, 17.31.

EXAMPLE 9

[(2-chloroethyl)thio]acetic acid

[Structure: Cl-CH₂CH₂-S-CH₂-CO₂H]

Mercaptoacetic acid (10.6 g, 0.11 mole) was added to ethyl alcohol (100 ml) containing sodium ethoxide freshly prepared from sodium (5.56 g, 0.24 mole). After stirring for 2.5 hours, 1-bromo-2-chloroethane (41.3 g, 0.288 mole) was added dropwise over three minutes and stirred overnight at room temperature. The white solid was filtered, dissolved in water (50 ml) and acidified with ten percent hydrochloric acid (50 ml) and extracted with ethyl acetate (3×50 ml). The extracts were combined, dried over sodium sulfate, filtered and concentrated to give an oil which was identified by NMR as the title compound.

EXAMPLE 10 methyl [(2-chloroethyl)thio]acetate

[Structure: Cl-CH₂CH₂-S-CH₂-CO₂CH₃]

Thionyl chloride (10 ml) was added to a solution of the title compound of Example 9 (9.7 g, 0.06 mole) in methyl alcohol (100 ml) cooled to 5° C. via an ice bath. The ice bath was removed and the reaction stirred for 2.5 hours at room temperature. The methyl alcohol and excess thionyl chloride were removed using a rotary evaporator to give 9.8 g, of an oil which was identified by NMR as the title compound.

EXAMPLE 11 methyl [(2-chloroethyl)sulfinyl]acetate

[Structure: Cl-CH₂CH₂-S(=O)-CH₂-CO₂CH₃]

3-Chloro-peroxybenzoic acid (81%, 4.7 g, 0.022 mole) was added to the title compound of Example 10 (3.7 g, 0.022 mole) in cold (5° C.) methylene chloride (75 ml) stirred for 30 minutes and cooled in a refrigerator for 48 hours. After removing the solid by filtration, a saturated solution of sodium thiosulfate (30 ml) was added and the mixture stirred for 15 minutes. The layers were separated and the organic layer was washed with saturated sodium bicarbonate (2×50 ml), dried over sodium sulfate, filtered and the solvent removed on a rotary evaporator. The residue was crystallized from ethyl acetate and hexane to give a white solid which was identified as the title compound by its NMR and IR spectra.

EXAMPLE 12 ethyl [[2-[[3,5-bis(1,1-dimethylethyl)-4-hydroxyphenyl]thio]ethyl]sulfinyl]acetate

[Structure: 2,6-di-tert-butyl-4-hydroxyphenyl-S-CH₂CH₂-S(=O)-CH₂-CO₂CH₂CH₃]

2,6-bis(1,1-Dimethylethyl)-4-mercaptophenol (2.97 g, 0.0125 mole) was added to sodium ethoxide, freshly prepared from sodium (0.29 g, 0.0125 mole) in ethyl alcohol (75 ml), and stirred for 1.5 hours. A solution of the title compound of Example 11 (2.3 g, 0.0125 mole) in ethyl alcohol (50 ml) was added dropwise over one hour and the resulting solution stirred for 20 hours at room temperature. Water (100 ml) was added and the ethyl alcohol removed using a rotary evaporator. The aqueous residue was extracted with ethyl acetate (2×100 ml). The combined organic extracts were dried over sodium sulfate, filtered, concentrated and the

EXAMPLE 13

3-[[2-[[3,5-bis(1,1-dimethylethyl)-4-hydroxyphenyl]thio]ethyl]thio]propanoic acid

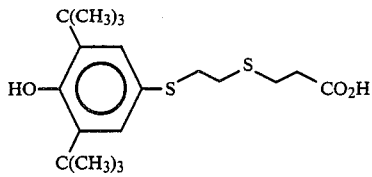

The title compound was prepared according to the method of Example 5 from 3-mercaptopropionic acid (6.1 g, 0.057 mole); sodium (3.9 g, 0.17 mole); 1-bromo-2-chloroethane (12.4 g, 0.086 mole); and 2,6-bis(1,1-dimethylethyl)-4-mercaptophenol (13.7 g, 0.057 mole), purified by chromatography on silica and recrystallized from ethyl acetate/hexane, m.p. ca. 57.5° C.

Analysis calc. for $C_{19}H_{30}O_3S_2$ (370.6): Calc.: C, 61.58; H, 8.16; S, 17.30. Found: C, 61.64; H, 7.89; S, 17.32.

EXAMPLE 14

4-[[2-[[3,5-bis(1,1-dimethylethyl)-4-hydroxyphenyl]thio]ethyl]thio]butanoic acid

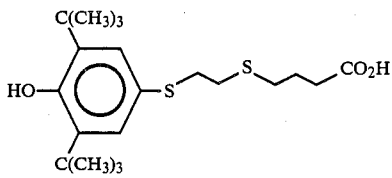

The title compound was prepared by the method of Example from 4-mercaptobutyric acid and identified by its NMR spectrum.

EXAMPLE 15 methyl 4-[[2-[[3,5-bis(1,1-dimethylethyl)-4-hydroxyphenyl]thio]ethyl]thio]butanoate

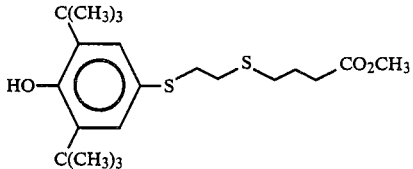

The title compound was prepared according to the method of Example 8 from the title compound of Example 14 (6.5 g) and thionyl chloride (10 ml) in methyl alcohol (75 ml).

Analysis calc. for $C_{21}H_{34}O_3S_2$ (398.6): Calc.: C, 63.28; H, 8.60; S, 16.09. Found: C, 63.49; H, 8.71; S, 16.14.

product purified by chromatography on silica. The yellow solid was recrystallized from ethyl acetate/hexane to give 1.1 g, m.p. ca. 110° C.

Analysis calc. for $C_{20}H_{32}O_4S_2$ (400.6): Calc.: C, 59.97; H, 8.05; S, 16.01. Found: C, 59.96; H, 7.72; S, 16.19.

EXAMPLE 16 methyl [(2-chloroethyl)sulfonyl]acetate

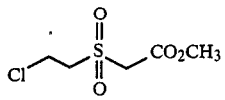

The title compound was prepared from 3-chloroperoxybenzoic acid and the title compound of Example 11 according to the procedure of Example 11 and identified by its NMR and IR spectra.

EXAMPLE 17 ethyl [[2-[[3,5-bis(1,1-dimethylethyl)-4-hydroxyphenyl]thio]ethyl]sulfonyl]acetate

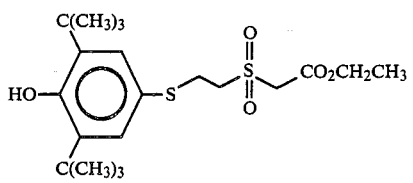

The title compound was prepared according to the method of Example 12 from the title compound of Example 16, sodium ethoxide and 2,6-bis(1,1-dimethylethyl)-4-mercaptophenol, m.p. ca. 95° C.

Analysis calc. for $C_{20}H_{32}O_5S_2$ (416.6): Calc.: C, 57.66; H, 7.74; S, 15.39. Found: C, 57.67; H, 7.77; S, 15.67.

EXAMPLE 18

2,6-bis(1,1-dimethylethyl)-4-[(2-hydroxy-1-methylpropyl)thio]phenol

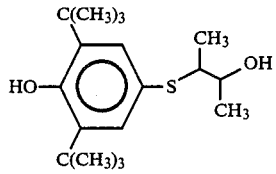

2,6-bis(1,1-Dimethylethyl)-4-mercaptophenol (18.2 g, 0.076 mole) was added to a solution of sodium ethoxide freshly prepared from sodium (3.5 g, 0.15 mole) in ethyl alcohol (100 ml) and stirred for 1 hour. After cooling to 5° C. with an ice bath, trans-2,3-epoxybutane (5.0 g, 0.069 mole) was added and the ice bath removed. After stirring for 5.5 hours the reaction mixture was poured into ten percent hydrochloric acid (50 ml). The ethyl alcohol was removed using a rotary evaporator and the aqueous residue extracted with ethyl acetate (2×75 ml). The extracts were combined, dried over sodium sulfate, filtered, and concentrated to an orange oil. The product was purified by chromatography on silica to give a yellow solid which was recrystallized from hexane to give a white solid, m.p. ca. 73° C.

Analysis calc. for $C_{18}H_{30}O_2S$ (310.5): Calc.: C, 69.63; H, 9.74; S, 10.33. Found: C, 69.75; H, 9.60; S, 10.35.

EXAMPLE 19 methyl
[[2-[[3,5-bis(1,1-dimethylethyl)-4-hydroxyphenyl]thio]-
1-methylpropyl]thio]acetate

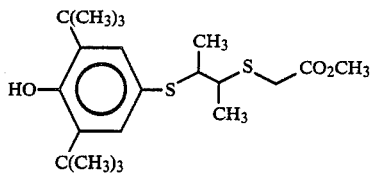

The title compound of Example 18 (3.5 g, 0.0122 mole) was added to trifluoroacetic acid (4 ml) and stirred for one hour. The methyl thioglycolate (1 ml, 0.0112 mole) was added, the reaction stirred for 2.5 hours and then poured into water (100 ml) and ethyl acetate (25 ml). After 18 hours the layers were separated and the organic layer concentrated to give 5.6 g of an oil. The product was purified by chromatography on silica.

Analysis calc. for $C_{21}H_{34}O_3S_2$ (398.1): Calc.: C, 63.28; H, 8.60; S, 16.09. Found: C, 63,17; H, 8.70; S, 16.15.

EXAMPLE 20

[[2-[[3,5-bis(1,1-dimethylethyl)-4-hydroxyphenyl]thio]-
1-methylpropyl]thio]acetic acid

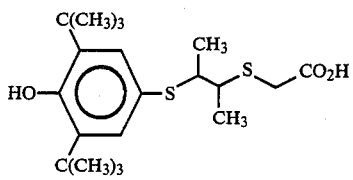

Lithium hydroxide monohydrate (0.20 g, 0.0035 mole) was added to a solution of the title compound of Example 19 (1.16 g, 0.0029 mole) in methyl alcohol (35 ml) and water (10 ml). When the reaction became clear more water was added. The reaction was acidified with ten percent hydrochloric acid. The methyl alcohol was removed using a rotary evaporator and the residue extracted with ethyl acetate. The ethyl acetate extract was dried over sodium sulfate, filtered and concentrated. The product was purified by chromatography on silica.

Analysis calc. for $C_{20}H_{32}O_3S_2$ (384.6): Calc.: C, 62,46; H, 8.39; S, 16.67. Found: C, 62.33; H, 8.22; S, 16.37.

EXAMPLE 21

2,6-bis(1,1-dimethylethyl)-4-[(2-hydroxy-2-methylpropyl)thio]phenol

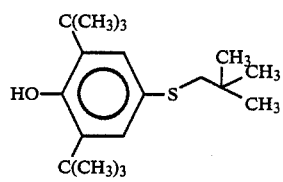

The title compound was prepared according to the method of Example 18 from 1,1-dimethylethylene oxide.

Analysis calc. for $C_{18}H_{30}O_2S$ (310.5): Calc.: C, 69.63; H, 9.74; S, 10.33. Found: C, 69.55; H, 9.92; S, 10.45.

EXAMPLE 22 methyl[[2-[[3,5-bis(1,1-dimethylethy)-4-hydroxyphenyl]thio]-2-methylpropyl]thio]acetate

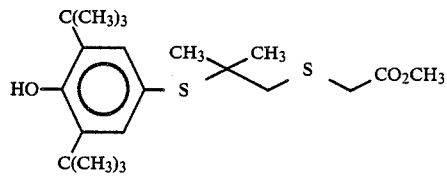

Methyl thioglycolate (0.7 g, 0.0067 mole) was added by syringe to a stirred solution of the title compound of Example 21 (2.2 g, 0.007 mole) and trifluoroacetic acid (3 ml). This solution after 3 hours was poured into water (50 ml) and extracted with ethyl acetate (2×50 ml). The extracts were combined, dried over sodium sulfate, filtered and concentrated to an oil. The product was purified by chromatography on silica. The product of Example 25 is also obtained in this reaction as the methyl ester.

Analysis calc. for $C_{21}H_{34}O_3S_2$ (398.6): Calc.: C, 63.27; H, 8.60; S, 16.09. Found: C, 63.00; H, 8.61; S, 16.19.

EXAMPLE 23

2,6-bis(1,1-dimethylethyl)-4-[(2-hydroxypropyl)thio]-
phenol

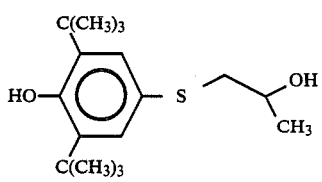

The title compound was prepared according to the method of Example 18 from propylene oxide, m.p. ca. 82° C.

Analysis calc. for $C_{17}H_{28}O_2S$ (296.5): Calc.: C, 68.87; H, 9.52; S, 10.82. Found: C, 69.10; H, 9.49; S, 11.06.

EXAMPLE 24 ethyl[(2-hydroxy-2-methylpropyl)thio]acetate

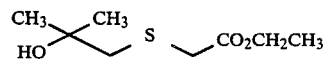

The title compound was prepared according to the method of Example 18 from methyl thioglycolate (13.8 g, 0.13 mole), sodium (3.0 g, 0.13 mole) and 1,1-dimethylethylene oxide (9.3 g, 0.13 mole). The title compound was identified by its NMR spectrum.

EXAMPLE 25 ethyl[[2-[[3,5-bis(1,1-dimethylethyl)-4-hydrroxyphenyl]thio]-1,1-dimethylethyl]thio]acetate

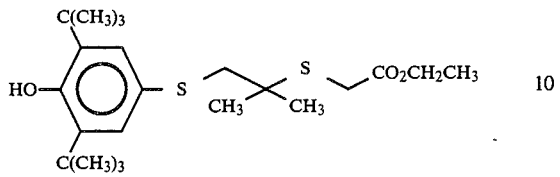

Trifluoroacetic acid (10 ml) was added to a solution of 2,6-bis(1,1-dimethylethyl)-4-mercaptophenol (2.6 g, 0.011 mole) and the title compound of Example 24 (1.9 g, 0.01 mole) in methylene chloride (50 ml) and stirred for 20 hours at room temperature. The reaction was poured into water (100 ml) and the layers separated. The organic layer was washed with water (100 ml), dried over sodium sulfate, filtered and concentrated. The product (an oil) was purified by chromatography on silica and identified by $^1$H NMR and $^{13}$C NMR spectra. The product of Example 22 is also obtained in this reaction as the ethyl ester.

EXAMPLE 26 methyl[[2-[[3,5-bis(1,1-dimethylethyl)-4-hydroxyphenyl]thio]propyl]thio]acetate and
methyl[[2-[[3,5-bis(1,1-dimethylethyl)-4-hydroxyphenyl]thio-1-methylethyl]thio]acetate

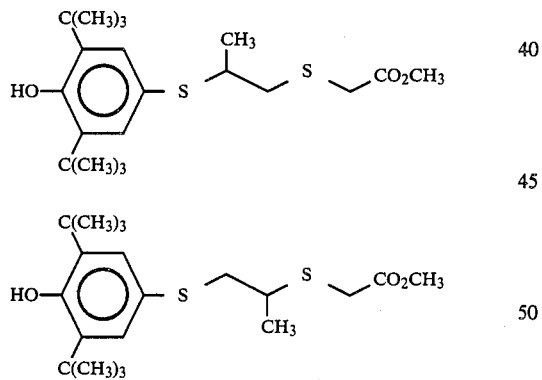

Methyl thioglycolate (1 ml, 0.0112 mole) was added to a solution of the title compound of Example 23 (3.5 g, 0.0118 mole) in trifluoroacetic acid (3 ml). The solution was stirred for 48 hours, poured into water (50 ml) and extracted with ethyl acetate (50 ml). The ethyl acetate extract was washed with water (2×50 ml), saturated sodium bicarbonate (50 ml), water (2×50 ml), dried over sodium sulfate, filtered and concentrated to give an oil. The products (oil) were purified by chromatography on silica.

Analysis calc. for $C_{20}H_{32}S_2O_3$ (384.6): Calc.: C, 62.46; H, 8.39; S, 16.67. Found: C, 62.63; H, 8.29; S, 16.80.

EXAMPLE 27

2'-hydroxy[1,1':3',1''-terphenyl]-5'-yl thiocyanate

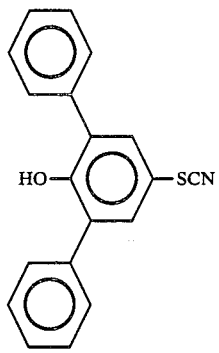

2,6-Diphenylphenol (100 g, 0.406 mole) and ammonium thiocyanate (67.99 g, 0.893 mole) were suspended in methanol (150 ml) in a three necked round bottom flask equipped with magnetic stirrer, thermometer and bubbler. The reaction mixture was cooled to −5° C. in an acetone/ice bath and chlorine gas bubbled through the solution for three hours. Maintaining the temperature below 10° C., ammonia gas was bubbled through the reaction for 2 hours. The contents of the flask were then poured into iced distilled water (250 ml) and allowed to stand for 12 hours. After filtering, the solid was dried in vacuo at 45° C. for 12 hours. The title compound was purified by chromatography on silica and recrystallized from hexane, m.p. ca. 104°–106.5° C.

Analysis calc. for $C_{19}H_{13}OSN$ (303.69): Calc.: C, 75.22; H, 4.32; N, 4.62; S, 10.57. Found: C, 75.12; H, 4.49; N, 4.65; S, 10.41.

EXAMPLE 28

5'-mercapto-[1,1':3',1''-terphenyl]-2'-ol

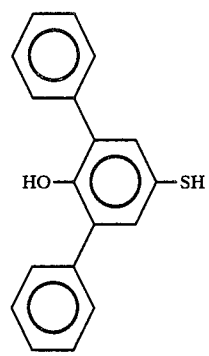

The title compound of Example 27 (32.2 g, 0.106 mole) and water (1.9 ml) were dissolved in acetone (150 ml) with stirring and cooled to −5° C. Triethylphosphine (15.7 ml, 0.106 mole) was added dropwise over a period of 40 minutes. The reaction was stirred at 0° C. for 1 hour and then at room temperature for 2 hours. The solvent was evaporated and the product isolated by chromatography on silica.

Analysis calc. for $C_{18}H_{14}OS$ (278.31): Calc.: C, 77.67; H, 5.07; S, 11.52. Found: C, 77.80; H, 5.19; S, 11.68.

EXAMPLE 29

[[2-[(2'-hydroxy[1,1':3',1''-terphenyl]-5'-yl)thio]ethyl]thio]acetic acid

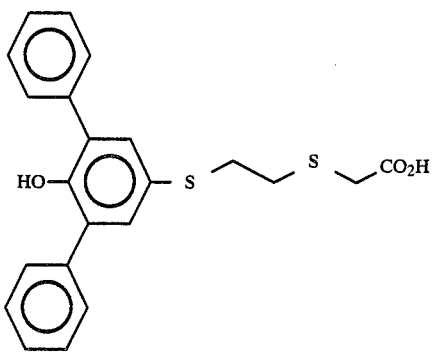

The title compound was prepared according to the method of Example 13 from mercaptoacetic acid (2.3 g, 0.025 mole); 1-bromo-2-chloroethane (2.1 ml, 0.025 mole); sodium (1.8 g, 0.08 mole) and 5'-mercapto-[1,1':3',1''-terphenyl]-2'-ol (8.6 g, 0.03 mole), m.p. ca. 125° C.

Analysis calc. for $C_{22}H_{20}O_3S_2$ (396.5): Calc.: C, 66.64; H, 5.08; S, 16.17. Found: C, 67.01; H, 5.13; S, 16.10.

EXAMPLE 30

2,6-bis(1,1-dimethylethyl)-4-[(2-hydroxyethyl)thio]phenol

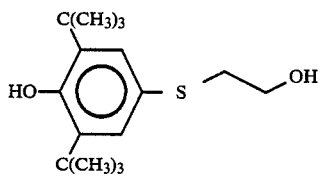

Triethylamine (0.42 g, 0.0042 mole), 2-bromoethanol (0.52 g, 0.0044 mole) and the title compound of Example 2 (1.0 g, 0.0042 mole) were stirred in methylene chloride (50 ml) for 20 hours. The reaction was condensed and ethyl acetate (25 ml) added to the residue. After filtering the white solid the filtrate was concentrated and the product purified by chromatography on silica, m.p. ca. 66° C.

Analysis calc. for $C_{16}H_{26}O_2S$ (282.4): Calc.: C, 68.04; H, 9.28; S, 11.35. Found: C, 67.98; H, 9.20; S, 11.24.

EXAMPLE 31

[2-[[3,5-bis(1,1-dimethylethyl)-4-hydroxyphenyl]thio]ethoxy]acetic acid

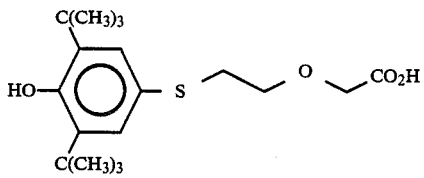

Chloroacetic acid (1.88 g) was added to a solution of the product of Example 30 (5.64 g) in tert. butyl alcohol. Potassium tert-butoxide (8.96 g) was added and the mixture refluxed for 22 hours. The reaction was made basic with 5% sodium bicarbonate and extracted with ethyl ether (3×50 ml). The NaHCO3 extracts were acidified to about pH 2 with 1N HCL and extracted 3 times with ethyl ether (100 ml). The combined organic extracts were washed twice with water, twice with saturated brine, dried over sodium sulfate and the solvent removed using a rotary evaporator to give the impure product. The product was purified by chromatography on silica, m.p. ca. 86° C.

Analysis calc. for $C_{18}H_{28}O_4S$ (340.47): Calc.: C, 63.50; H, 8.29; S, 9.42. Found: C, 63.52; H, 8.02; S, 9.46.

EXAMPLE 32

4-hydroxy-3-methylphenyl thiocyanate

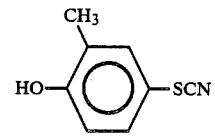

Sodium thiocyanate (23.5 g, 0.29 mole) was added to a solution of ortho-cresol (31.4 g, 0.29 mole) in methyl alcohol (225 ml) and cooled by an ice bath. A solution of bromine (46.4 g, 0.29 mole) in methyl alcohol (50 ml) was added dropwise over 45 minutes. The reaction was filtered and poured into water (400 ml). Sodium thiosulfate was added to eliminate the color (yellow). The product was extracted into ethyl ether (2×200 ml). The ethyl ether extracts were washed with water (100 ml), 1N hydrochloric acid (200 ml) and saturated sodium chloride (50 ml), dried over magnesium sulfate, filtered and concentrated. The product was purified by chromatography on silica. The structure was confirmed by NMR and IR spectroscopy.

EXAMPLE 33

4-mercapto-2-methylphenol

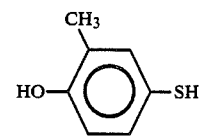

The title compound was prepared according to the method of Example 2 from triethylphosphine (10.0 g), water (1.5 g) and Example 32 (14.0 g). The structure was confirmed by NMR and IR spectroscopy.

EXAMPLE 34

[[2-[(4-hydroxy-3-methylphenyl)thio]ethyl]thio]acetic acid

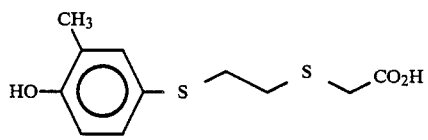

The title compound was prepared according to the method of Example 5 from the compound of Example 33, m.p. ca. 86° C.

Analysis calc. for $C_{11}H_{14}O_3S_2$ (258.3): Calc.: C, 51.13; H, 5.47; S, 24.82. Found: C, 51.09; H, 5.50; S, 24.86.

EXAMPLE 35

4-hydroxyphenyl thiocyanate

The title compound was prepared according to the method of Example 32 from phenol (0.35 mole), bromine (0.35 mole) and sodium thiocyanate (0.35 mole).

EXAMPLE 36

4-[(2-chloroethyl)thio]phenol

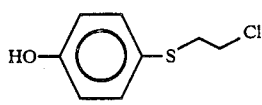

2-chloro-ethanol (3.9 g, 0.049 mole) was added to a solution of the product of Example 35 (7.4 g, 0.049 mole) in acetone (50 ml). After cooling with an ice bath triethylphosphine (5.6 g, 0.047 mole) was added dropwise over 25 minutes. Ethyl ether (200 ml) and water (75 ml) were added and the layers separated. The organic layer was washed with water (4×50 ml) and saturated sodium chloride (2×25 ml) dried over magnesium sulfate, filtered and concentrated to give a yellow oil. The structure was confirmed by its NMR spectrum.

EXAMPLE 37

[[2-[(4-hydroxyphenyl)thio]ethyl]thio]acetic acid

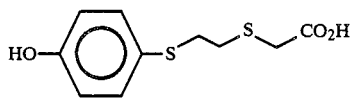

Mercaptoacetic acid (3.5 g, 0.039 mole) was added to ethyl alcohol (100 ml) containing sodium (1.8 g, 0.078 mole). The compound of Example 36 (7.3 g, 0.039 mole) in ethyl alcohol (20 ml) was added dropwise and the mixture refluxed 1 hour. The reaction mixture was cooled to room temperature, poured into water (250 ml) and acidified with 2N hydrochloric acid. The product was extracted into ethyl ether (2×150 ml) and the ethyl ether extracted with 1M sodium bicarbonate (3×80 ml). The combined basic washes were acidified with 2N hydrochloric acid and extracted with ethyl ether (3×150 ml). The combined ethyl ether extracts were washed with water (3×75 ml) and saturated sodium chloride (50 ml), dried over magnesium sulfate, filtered and concentrated to give a yellow solid. Recrystallization from ethyl ether/pentane gave the title compound, m.p. ca. 105° C.

Analysis calc. for $C_{10}H_{12}O_3S_2$ (244.3): Calc.: C, 49.15; H, 4.96; S, 26.24. Found: C, 49.02; H, 5.00; S, 26.41.

EXAMPLE 38

3-[[3,5-bis(1,1-dimethylethyl)-4-hydroxyphenyl]thio]propanal

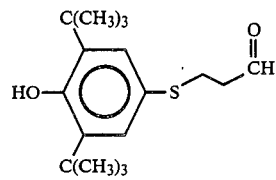

Triethylamine (1.1 ml, 0.0076 mole) was added to a solution of 2,6-bis(1,1-dimethylethyl)-4-mercaptophenol (18.2 g, 0.076 mole) in methyl alcohol (200 ml) and stirred for 30 minutes. Freshly distilled acrolein (12.8 g, 0.23 mole) was added and the solution stirred at room temperature. The product was purified by chromatography on silica and characterized by its NMR and IR spectra and m.p. ca. 75° C.

EXAMPLE 39 ethyl[[3-[[3,5-bis(1,1-dimethylethyl)-4-hydrroxyphenyl]thio]propyl]methylamino]acetate

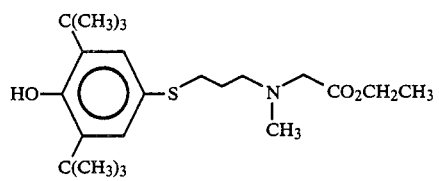

Sarcosine ethyl ester hydrochloride (2.3 g, 0.015 mole) and the compound of example 38 (5.0 g, 0.017 mole) were stirred two hours in ethyl alcohol (40 ml). Sodium cyanoborohydride (0.93 g, 0.015 mole) was added and the mixture stirred at room temperature for 18 hours, refluxed for 30 minutes, then acidified with 1N hydrochloric acid to about pH 2. After stirring for 1 hour the volume of the reaction mixture was concentrated, water (50 ml) added and the product extracted with ethyl acetate. The ethyl acetate extract was washed with water and saturated sodium chloride and dried over magnesium sulfate, filtered and concentrated. The product was purified by chromatography on silica.

Analysis calc. for $C_{22}H_{37}O_3NS$ (395.6): Calc.: C, 66.79; H, 9.43; N, 3.54; S, 8.10. Found: C, 67.09; H, 9.40; N, 3.50; S, 8.21.

EXAMPLE 40 methyl[[3-[[3,5-bis(1,1-dimethylethyl)-4-hydroxyphenyl]thio]propyl]methylamino]acetate, monohydrochloride

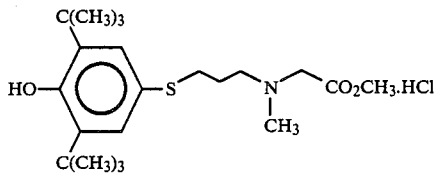

Gaseous hydrogen chloride was bubbled into a solution of the compound of Example 39 (113 mg) in methyl alcohol (20 ml) for 15 minutes and the reaction stirred for four days. The reaction was concentrated and the product was characterized by its NMR and IR spectra.

EXAMPLE 40A

[[3-[[3,5-bis(1,1-Dimethylethyl-4-hydroxyphenyl]thio]-propyl]methyl]amino]acetic acid, monohydrochloride

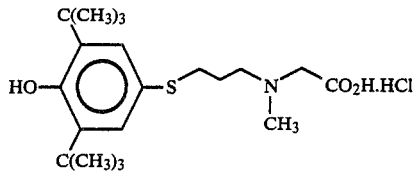

The product from Example 39 was hydrolysed with 6N hydrochloric acid at 65° C. to give the title compound, m.p. ca. 168° C.

Analysis calc. for $C_{20}H_{33}O_3NS.HCl$ (403.22): Calc: C, 59.46; H, 8.48; N, 3.47; Cl, 8.78, S, 7.94. Found: C, 59.17; H, 8.40; N, 3.22; Cl, 8.86; S, 8.09.

EXAMPLE 41

[[3-[[3,5-bis(1,1-dimethylethyl)-4-hydroxyphenyl]thio]-2-hydroxypropyl]thio]acetic acid

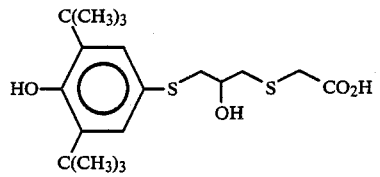

Mercaptoacetic acid (1.32 g, 0.0144 mole) was added to a solution of ethyl alcohol (100 ml) containing sodium (0.66 g, 0.029 mole). The solution was stirred for 30 minutes and epichlorohydrin (1.33 g, 0.0144 mole) was added by syringe. A solution of the sodium salt of 2,6-bis(1,1-dimethylethyl)-4-mercaptophenol prepared from 2,6-bis(1,1-dimethylethyl)-4-mercaptophenol (3.43 g, 0.0144 mole) and sodium (0.33 g, 0.0144 mole) in ethyl alcohol (50 ml) was added dropwise and the reaction stirred for 72 hours at room temperature. Water (50 ml) was added and the ethyl alcohol removed using a rotary evaporator. The product was extracted into ethyl acetate, dried over sodium sulfate, filtered and concentrated. The product was isolated as an oil by chromatography on silica. The structure was confirmed by its NMR and IR spectra.

EXAMPLE 42 methyl[[3-[[3,5-bis(1,1-dimethylethyl)-4-hydroxyphenyl]thio]-2-hydroxypropyl]thio]acetate

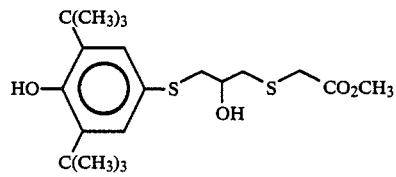

Oxalyl chloride (3 ml) was added to a solution of the compound of Example 41 (2.3 g) in benzene (50 ml) and stirred for 3 hours at room temperature. The reaction volume was reduced and methyl alcohol (100 ml) added. After evaporation of the solvents, the product (an oil) was purified by chromatography on silica.

Analysis calc. for $C_{20}H_{32}O_4S_2$ (400.6): Calc.: C, 59.97; H, 8.05; S, 16.01. Found: C, 59.64; H, 8.15; S, 16.08.

Utilizing the foregoing synthesis methods and appropriate starting materials, the following compounds are likewise obtained:

EXAMPLE 43

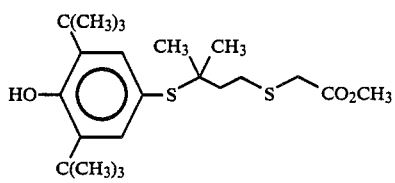

EXAMPLE 44

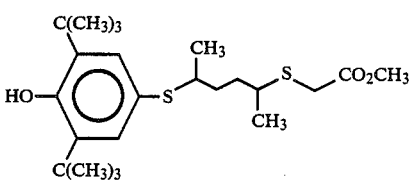

EXAMPLE 45

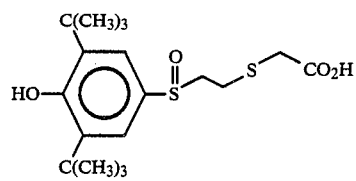

EXAMPLE 46

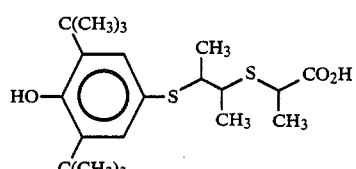

EXAMPLE 47

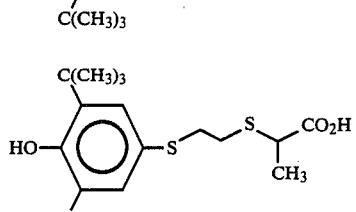

EXAMPLE 48

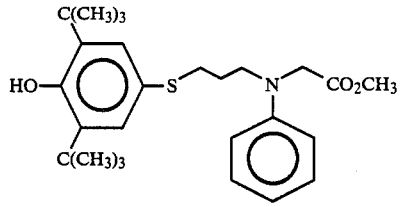

EXAMPLE 49

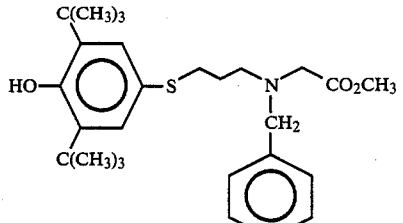

EXAMPLE 50

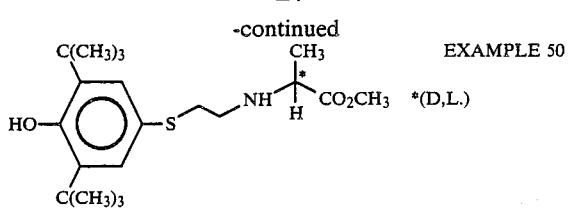

EXAMPLE 51

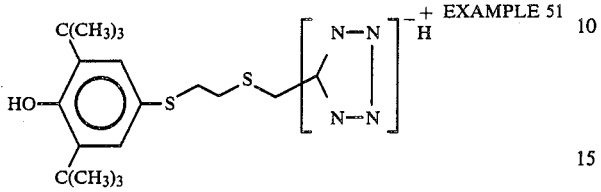

BIOLOGICAL EVALUATIONS

The compounds of the invention are evaluated with respect to 5-lipoxygenase inhibition according to the following assay procedures.

(1) Inhibition of 5-lipoxygenase, in vitro: anti-inflammatory, anti-allergy activities.

The $100,000 \times g$ supernatant fraction of Rat Basophilic Leukemia Cell Homogenate (RBL-1) serves as a 5-lipoxygenase enzyme source. The enzyme is incubated with $[1-^{14}C]$-arachidonic acid and $Ca++$ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}M$. When the compound inhibits more than 50% of 5-HETE synthesis at $10^{-4}M$, that compound is tested at multiple dose levels to determine the $IC_{50}$ value (inhibitory concentration to inhibit 50%).

(2) In vivo inhibition of ovalbumin-induced bronchoconstriction—Anti-allergy assay.

Adult, male Hartley guinea pigs (300–350 g, fasted) actively sensitized to ovalbumin are utilized in this assay.

Ovalbumin (OA) causes bronchoconstriction when administered to actively-sensitized guinea pigs. The observed bronchoconstruction is comprised of at least two distinct components:

(a) a cyclooxygenase-dependent, rapidly occurring bronchoconstriction mediated by thromboxane $A_2$ and possibly other mediators and (b) a 5-lipoxygenase dependent slow developing component, dependent upon the de-novo generation of $LTC_4$ and $LTD_4$.

All test animals are pretreated with aspirin and pyrilamine to block the occurrence of the rapidly occurring component (a). Compounds which block the generation of $LTC_4$ and $LTD_4$ (5-lipoxygenese inhibitors) or antagonize the activity of $LTC_4/LTD_4$ (leukotriene inhibitors) modulate the severity of the remaining component of this well-characterized anaphylactic response.

Test compounds are administered at screening doses of 50 mg/kg, i.v., or 100 mg/kg, i.g. A compound is rated active in this test if it causes a significant reduction (i.e., $p \leq 0.05$, student's t-test) in intratracheal insufflation pressure induced by an i.v. injection of ovalbumin (3 mg/ml, i.v.), aspirin (5 mg/kg. i.v.) and propranolol (6 mg/kg i.p.). Treated animals are statistically compared to concurrent vehicle treated controls. Compounds rated active in inhibiting the production of the $LTC_4/LTD_4$ allergic mediators through inhibition of 5-lipoxygenase according to this test are believed to play a significant role in bronchopulmonary allergic conditions, e.g., asthma.

The results with respect to certain of the preferred compounds of the present invention are set forth in Tables I and II below:

TABLE I

| Compound Example No. | 5-Lipoxygenase Inhibition, in vitro, $IC_{50}(\mu M)$ |
| --- | --- |
| 4 | 1.40 |
| 6 | 1.80 |
| 12 | 0.33 |
| 13 | 1.00 |
| 15 | 0.12 |
| 17 | 0.30 |
| 19 | 0.24 |
| 20 | 0.82 |
| 31 | 7.30 |
| 34 (Comparative Compound) | ≈100 |
| 37 (Comparative Compound) | 55.0 |
| 42 | 0.31 |

TABLE II

| Compound Example No. | Antagonism of OA-induced bronchoconstriction in the Guinea Pig, (min. effective dose) |
| --- | --- |
| 3 | ≦100 mg/kg, i.g. @ 3 hr. (vehicle 1) |
| 6 | ≦50 mg/kg, i.g. @ 3 hr. (vehicle 1) |
| 4 | ≦100 mg/kg, i.g. @ 3 hr. (vehicle 2) |
| 8 | ≦100 mg/kg, i.g. @ 3 hr. (vehicle 1) |
| 13 | ≦100 mg/kg, i.g. @ 5 hr. (vehicle 2) |
| 19 | ≦32 mg/kg, i.g. @ 3 hr. (vehicle 2) |
| 20 | ≦32 mg/kg, i.g. @ 3 hr. (vehicle 2) |
| 34 | >100 mg/kg, i.g. @ 3 hr. (vehicle 2) |
| 37 | >100 mg/kg, i.g. @ 3 hr. (vehicle 2) |
| 42 | ≦50 mg/kg, i.g. @ 2 hr. (vehicle 1) |

Vehicle 1 = 20% DMSO in polyethylene glycol
Vehicle 2 = peanut oil

It is further noted that the compounds of the present invention have not been found to be inhibitors of either 12- or 15-lipoxygenases or of cyclooxygenase at concentrations which inhibit 5-lipoxygenase further confirming the specificity of the present compounds for 5-lipoxygenase.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological response observed may vary depend-

What is claimed is:

1. A compound of the formula:

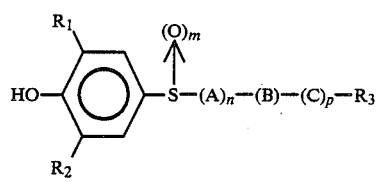

or a pharmaceutically acceptable salt thereof wherein $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, phenyl substituted by one or two substituents which may be the same or different and are independently selected from the group consisting of halogen, $C_1$-$C_6$ alkyl, hydroxy, $C_1$-$C_6$-alkoxy, acetoxy, carboxylic acid and $C_1$-$C_6$ alkyl esters thereof, nitro or phenyl or benzyl substituted by one or two substituents which may be the same or different and are independently selected from the group consisting of halogen, $C_1$-$C_6$ alkyl, hydroxy, $C_1$-$C_6$ alkoxy, acetoxy, carboxylic acid and $C_1$-$C_6$ alkyl esters thereof, nitro or phenyl; C represents methylene or methylene substituted by alkyl; $R_3$ represents $CO_2H$, $CO_2$-alkyl, or a tetrazole group; m is 0 or 1, n is 2, 3, or 4 and p is 1, 2, or 3.

2. A compound according to claim 1 wherein $R_1$ and $R_2$ are both tert-alkyl.

3. A compound according to claim 2 wherein said tert-alkyl is tert-butyl.

4. A compound according to claim 1 wherein $R_1$ and $R_2$ are both phenyl.

5. A compound according to claim 1 wherein $(A)_n$ is —$CH_2$—$CH_2$— or —$CH_2$—CH(OH)—$CH_2$—.

6. A compound according to claim 1 wherein B is sulfur, sulfoxide or sulfone.

7. A compound according to claim 1 wherein B is oxygen, —NH— or nitrogen substituted by alkyl, phenyl, benzyl, substituted phenyl or substituted benzyl.

8. A compound according to claim 1 wherein C is —$CH_2$—.

9. A compound according to claim 1 wherein $R_3$ is —$CO_2H$.

10. A compound according to claim 1 wherein said compound is of the formula:

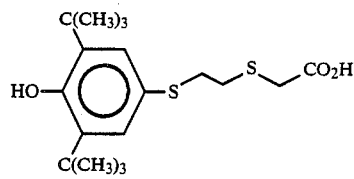

11. A pharmaceutical composition for the treatment of inflammation and allergy conditions comprising a therapeutically effective amount of a compound according to claim 1 and a pharmaceutically acceptable carrier.

12. A pharmaceutical composition according to claim 11 adapted for oral administration.

13. A pharmaceutical composition according to claim 11 adapted for aerosol administration.

14. A pharmaceutical composition according to claim 11 adapted for parenteral administration.

15. A pharmaceutical composition according to claim 14 wherein said parenteral administration is intravenous administration.

16. A method of eliciting an anti-inflammatory or anti-allergic effect in a mammal in need thereof comprising administering thereto a therapeutically effective amount of a compound according to claim 1.

17. A method of treating asthma in a mammal in need thereof comprising administering thereto a therapeutically effective amount of a compound according to claim 1.

18. A method of treating proliferative skin disorders in a mammal in need thereof comprising administering thereto a therapeutically effective amount of a compound according to claim 1.

19. A method according to claim 15 wherein said compound is administered topically.

20. A method of inhibiting 5-lipoxygenase in a mammal in need thereof comprising administering thereto a therapeutically effective amount of a compound according to claim 1.

* * * * *

UNITED STATES PATENT AND TRADEMARK OFFICE
CERTIFICATE OF CORRECTION

PATENT NO. : 4,711,903
DATED : December 8, 1987
INVENTOR(S) : Mueller, et al.

It is certified that error appears in the above-identified patent and that said Letters Patent are hereby corrected as shown below:

Column 15, line 45, reading "Example from" should read -- Example 13 from --.

Column 17, lines 15-16, reading "0.0122 mole)" should read -- 0.0112 mole) --.

Column 17, the third structure, that portion of the structure reading

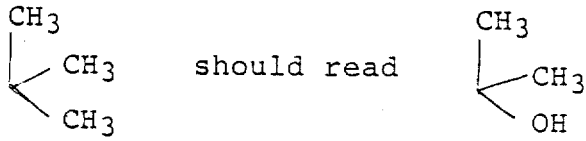

UNITED STATES PATENT AND TRADEMARK OFFICE
CERTIFICATE OF CORRECTION

PATENT NO. : 4,711,903

DATED : December 8, 1987

INVENTOR(S) : Mueller, et al.

It is certified that error appears in the above-identified patent and that said Letters Patent is hereby corrected as shown below:

Column 27, the second structure, that portion of the structure reading

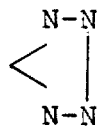   should read   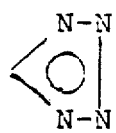

Signed and Sealed this

Twenty-ninth Day of November, 1988

Attest:

DONALD J. QUIGG

Attesting Officer   Commissioner of Patents and Trademarks